United States Patent [19]
Miyazaki et al.

[11] Patent Number: 5,770,400
[45] Date of Patent: Jun. 23, 1998

[54] EXOGENOUS GENE EXPRESSION VECTOR CONTAINING CHICK β-ACTIN GENE PROMOTER

[75] Inventors: Junichi Miyazaki; Ken-ichi Yamamura; Masatake Araki; Hiroshi Yonemura; Chikateru Nozaki, all of Kumamoto, Japan

[73] Assignee: Juridical Foundation The Chemo-Sero-Therapeutic Research Institute, Kumamoto, Japan

[21] Appl. No.: 814,468

[22] Filed: Mar. 10, 1997

Related U.S. Application Data

[63] Continuation of Ser. No. 373,143, Jun. 23, 1989.

[30] Foreign Application Priority Data

Jun. 24, 1988 [JP] Japan .................................. 63-157569
Dec. 9, 1988 [JP] Japan .................................. 63-312444

[51] Int. Cl.⁶ .......................... C12N 15/70; C12N 15/85; C12P 21/02
[52] U.S. Cl. .................. 435/69.1; 435/320.1; 435/240.2; 935/23; 935/27
[58] Field of Search ............................... 435/69.1, 320.1, 435/70.1, 172.1, 252.33; 935/24, 32, 34, 38, 66

[56] References Cited

U.S. PATENT DOCUMENTS 4,740,461  4/1988  Kaufman .................................. 435/69.1

FOREIGN PATENT DOCUMENTS 174 608   3/1986  European Pat. Off. .
87-03905  7/1987  WIPO .

OTHER PUBLICATIONS

Kost et al., Nucleic Acids Research, vol. 11(23):8287–8300, (1983).
Fregien et al., "Activating Elements In The Promoter Region Of The Chicken β–Actin Gene", *Gene*, vol. 48:1–11, (1986).
Guild et al., "Development of Retrovirus Vectors Useful For Expressing Genes In Cultured Murine Embryonal Cells And Hematopoietic Cells In Vivo", *J. of Virology*, pp. 3795–3801, (1988).
Quitschke et al., "The β–Actin Promoter", *J. of Biological Chemistry*, vol. 264(16):9539–9546, (1989).

*Primary Examiner*—Stephanie W. Zitomer
*Attorney, Agent, or Firm*—Foley & Lardner

[57] ABSTRACT

An expression vector for the expression of an exogenous gene in an animal cell, which contains a chick β-actin gene promoter and a restriction enzyme site for incorporating an exogenous gene at the downstream of said promoter and a process for expressing an exogenous gene, which comprises incorporating said exogenous gene into the expression vector at the restriction enzyme site for incorporating the exogenous gene, introducing said vector into an animal cell and culturing the obtained transformed animal cell. The expression system of the present invention can be applied to an expression of any exogenous gene and has an extremely high expression efficiency and is applicable to a wide range of host cells, and hence can sufficiently be utilized for industrial-scale production of a useful material.

11 Claims, 18 Drawing Sheets

FIG. 1-(1)

```
       -1271      -1261      -1251      -1241
       TCGAG GTGAGCCCCA CGTTCTGCTT CACTCTCCCC

-1231      -1221      -1211      -1201
    ATCTCCCCCC CCTCCCCACC CCCAATTTTG TATTTATTTA

-1191      -1181      -1171      -1161
    TTTTTTAATT ATTTTGTGCA GCGATGGGGG CGGGGGGGGG

-1151      -1141      -1131      -1121
    GGGGGCGCGC GCCAGGCGGG GCGGGGCGGG GCGAGGGGCG

-1111      -1101      -1091      -1081
    GGGCGGGGCG AGGCGGAGAG GTGCGGCGGC AGCCAATCAG

-1071      -1061      -1051      -1041
    AGCGGCGCGC TCCGAAAGTT TCCTTTTATG GCGAGGCGGC

-1031      -1021      -1011      -1001
    GGCGGCGGCG GCCCTATAAA AAGCGAAGCG CGCGGCGGGC

-991       -981       -971       -961
    GGGAGTCGCT GCGTTGCCTT CGCCCCGTGC CCCGCTCCGC

-951       -941       -931       -921
    GCCGCCTCGC GCCGCCCGCC CCGGCTCTGA CTGACCGCGT

-911       -901       -891       -881
    TACTCCCACA GGTGAGCGGG CGGGACGGCC CTTCTCCTCC

-871       -861       -851       -841
    GGGCTGTAAT TAGCGCTTGG TTTAATGACG GCTCGTTTCT
```

FIG. 1-(2)

```
        -831        -821        -811        -801
    TTTCTGTGGC  TGCGTGAAAG  CCTTAAAGGG  CTCCGGGAGG

-791        -781        -771        -761
    GCCCTTTGTG  CGGGGGGGAG  CGGCTCGGGC  GGTGCGTGCG

-751        -741        -731        -721
    TGTGTGTGTG  CGTGGGGAGC  GCCGCGTGCG  GCCCGCGCTG

-711        -701        -691        -681
    CCCGGCGGCT  GTGAGCGCTG  CGGGCGCGGC  GCGGGCTTT

-671        -661        -651        -641
    GTGCGCTCCG  CGTGTGCGCG  AGGGGAGCGC  GGCCGGGGGC

-631        -621        -611        -601
    GGTGCCCCGC  GGTGCGGGGG  GGCTGCGAGG  GGAACAAAGG

-591        -581        -571        -561
    CTGCGTGCGG  GGTGTGTGCG  TGGGGGGGTG  AGCAGGGGGT

-551        -541        -531        -521
    GTGGGCGCGG  CGGTCGGGCT  GTAACCCCCC  CCTGCACCCC

-511        -501        -491        -481
    CCTCCCCGAG  TTGCTGAGCA  CGGCCCGGCT  TCGGGTGCGG

-471        -461        -451        -441
    GGCTCCGTGC  GGGGCGTGGC  GCGGGGCTCG  CCGTGCCGGG

-431        -421        -411        -401
    CGGGGGGTGG  CGGCAGGTGG  GGGTGCCGGG  CGGGGCGGGG
```

FIG. 1-(3)

```
        -391        -381        -371        -361
   CCGCCTCGGG  CCGGGGAGGG  CTCGGGGGAG  GGGCGCGGCG

-351        -341        -331        -321
   GCCCCGGAGC  GCCGGCGGCT  GTCGAGGCGC  GGCGAGCCGC

-311        -301        -291        -281
   AGCCATTGCC  TTTTATGGTA  ATCGTGCGAG  AGGGCGCAGG

-271        -261        -251        -241
   GACTTCCTTT  GTCCCAAATC  TGGCGGAGCC  GAAATCTGGG

-231        -221        -211        -201
   AGGCGCCGCC  GCACCCCTC  TAGCGGGCGC  GGGCGAAGCG

-191        -181        -171        -161
   GTGCGGCGCC  GGCAGGAAGG  AAATGGGCGG  GGAGGGCCTT

-151        -141        -131        -121
   CGTGCGTCGC  CGCGCCGCCG  TCCCCTTCTC  CATCTCCAGC

-111        -101         -91         -81
   CTCGGGGCTG  CCGCAGGGGG  ACGGCTGCCT  TCGGGGGGGA

-71         -61         -51         -41
   CGGGGCAGGG  CGGGGTTCGG  CTTCTGGCGT  GTGACCGGCG

-31         -21         -11          -1
   GGGTTTATAT  CTTCCCTTCT  CTGTTCCTCC  GCAGCCAGCC(ATG)
            ↑         ─────────
    MboⅡ cleavage site   MboⅡ recognition site
```

FIG. 2

```
CCATGG
GGTACC
```

FIG. 3

```
C
GGTAC
```

FIG. 4

```
            -51            -41            -31            -21            -11            -1
         CTTCTGGCGT GTGACCGGCG GGTTTATAT CTTCCCTTCT CTGTTCCTCC GCAGCCAGCC ATG GAT GAT...
                         β-actin promoter region                          β-actin structural gene plasmid p28   CTTCTGGCGT GTGACCGGCG GGTTTATAT CTTCCCTTCT CTGTTCCTCC GCAGCCAGCCAAGCTTGG
                                                                                 HindIII linker
```

FIG. 5-(1)

```
          -1271       -1261       -1251       -1241
          TCGAG  GTGAGCCCCA  CGTTCTGCTT  CACTCTCCCC

-1231       -1221       -1211       -1201
     ATCTCCCCCC  CCTCCCCACC  CCCAATTTTG  TATTTATTTA

-1191       -1181       -1171       -1161
     TTTTTTAATT  ATTTGTGCA   GCGATGGGGG  CGGGGGGGGG

-1151       -1141       -1131       -1121
     GGGGCGCGC   GCCAGGCGGG  GCGGGGCGGG  GCGAGGGGCG

-1111       -1101       -1091       -1081
     GGGCGGGGCG  AGGCGGAGAG  GTGCGGCGGC  AGCCAATCAG

-1071       -1061       -1051       -1041
     AGCGGCGCGC  TCCGAAAGTT  TCCTTTTATG  GCGAGGCGGC

-1031       -1021       -1011       -1001
     GGCGGCGGCG  GCCCTATAAA  AAGCGAAGCG  CGCGGCGGGC

-991        -981        -971        -961
     GGGAGTCGCT  GCGTTGCCTT  CGCCCCGTGC  CCCGCTCCGC

-951        -941        -931        -921
     GCCGCCTCGC  GCCGCCCGCC  CCGGCTCTGA  CTGACCGCGT

-911        -901        -891        -881
     TACTCCCACA  GGTGAGCGGG  CGGGACGGCC  CTTCTCCTCC

-871        -861        -851        -841
     GGGCTGTAAT  TAGCGCTTGG  TTTAATGACG  GCTCGTTTCT

-831        -821        -811        -801
     TTTCTGTGGC  TGCGTGAAAG  CCTTAAAGGG  CTCCGGGAGG
```

FIG. 5-(2)

```
         -791        -781        -771        -761
     GCCCTTTGTG  CGGGGGGGAG  CGGCTCGGGG  GGTGCGTGCG

-751        -741        -731        -721
     TGTGTGTGTG  CGTGGGGAGC  GCCGCGTGCG  GCCCGCGCTG

-711        -701        -691        -681
     CCCGGCGGCT  GTGAGCGCTG  CGGGCGCGGC  GCGGGCTTT

-671        -661        -651        -641
     GTGCGCTCCG  CGTGTGCGCG  AGGGGAGCGC  GGCCGGGGGC

-631        -621        -611        -601
     GGTGCCCGC   GGTGCGGGGG  GGCTGCGAGG  GGAACAAAGG

-591        -581        -571        -561
     CTGCGTGCGG  GGTGTGTGCG  TGGGGGGGTG  AGCAGGGGGT

-551        -541        -531        -521
     GTGGGCGCGG  CGGTCGGGCT  GTAACCCCCC  CCTGCACCCC

-511        -501        -491        -481
     CCTCCCCGAG  TTGCTGAGCA  CGGCCCGGCT  TCGGGTGCGG

-471        -461        -451        -441
     GGCTCCGTGC  GGGGCGTGGC  GCGGGGCTCG  CCGTGCCGGG

-431        -421        -411        -401
     CGGGGGGTGG  CGGCAGGTGG  GGGTGCCGGG  CGGGGCGGGG

-391        -381        -371        -361
     CCGCCTCGGG  CCGGGGAGGG  CTCGGGGGAG  GGGCGCGGCG

-351        -341        -331        -321
     GCCCCGGAGC  GCCGGCGGCT  GTCGAGGCGC  GGCGAGCCGC
```

FIG. 5-(3)

```
        -311        -301        -291        -281
   AGCCATTGCC TTTTATGGTA ATCGTGCGAG AGGGCGCAGG

-271        -261        -251        -241
   GACTTCCTTT GTCCCAAATC TGGCGGAGCC GAAATCTGGG

-231        -221        -211        -201
   AGGCGCCGCC GCACCCCCTC TAGCGGGCGC GGGCGAAGCG

-191        -181        -171        -161
   GTGCGGCGCC GGCAGGAAGG AAATGGGCGG GGAGGGCCTT

-151        -141        -131        -121
   CGTGCGTCGC CGCGCCGCCG TCCCCTTCTC CATCTCCAGC

-111        -101         -91         -81
   CTCGGGGCTG CCGCAGGGGG ACGGCTGCCT TCGGGGGGGA

Chick ß-actin gene ←─┐
        -71         -61         -51         -40
   CGGGGCAGGG CGGGGTTCGG CTTCTGGCGT GTGACCGGCGG
```

┌──→ β-globin gene
-CTCTAGAG-CCTCTGCTAACCATGTTCATGCCTTCTTCTTTT
   XbaI recognition site TCCTACAGCTCCTGGGCAACGTGCTGGTTGTTGTGCTGTCTCA
   ↑ splicing acceptor site TCATTTTGGCAAAGAATTCAAGCTT
               HindIII recognition site

EXOGENOUS GENE EXPRESSION VECTOR CONTAINING CHICK β-ACTIN GENE PROMOTER

CROSS-REFERENCE TO RELATED APPLICATIONS

This application is a continuation application of U.S. Ser. No. 07/373,143, filed Jun. 23, 1989.

The present invention relates to an expression vector for the expression of exogenous genes in animal cells, more particularly, relates to an expression vector which contains a chick β-actin gene promoter or a modified promoter thereof and is useful for expressing any exogenous gene efficiently in animal cells.

TECHNICAL BACKGROUND AND PRIOR ART

In recent years, with a progress of a gene engineering technique, a technique for producing a useful material by utilizing the gene engineering technique has rapidly been advanced. For expression of an exogenous gene utilizing the gene engineering technique, there are used a suitable host cell and an expression vector suited to the host cell employed. As the host cell for expression, there have hitherto been widely studied microorganisms which are easily handled such as *E. coli* and yeast. However, in recent years, it has been confirmed that the use of these microorganisms is limited in a certain degree in expression of a part of exogenous genes, and thus, an expression system which employs higher animal culture cells as the host cell has extensively been studied.

Such an expression system employing animal cells as the host cell has already been reported, including an expression system using a variety of an animal viral gene promoter or an animal cell gene promoter. The animal viral gene promoter includes, for example, an SV 40 gene promoter, an adenovirus major late gene promoter, a hepatitis B virus gene promoter, and the like. The animal cell gene promoter includes, for example, a thymidinekinase (tk) gene promoter, a metallothionein gene promoter, an interferon gene promoter, an immunoglobulin gene promoter, and the like.

Among the above promoters, it has been found that especially the SV 40 early gene promoter, the SV 40 late gene promoter and the adenovirus major late gene promoter have a powerful promoter activity. However, it is still insufficient for an industrial scale production and more powerful and highly expressionable promoter has been explored.

BRIEF SUMMARY OF THE INVENTION

Under such circumstances, the present inventors have intensively studied to develop an expression vector which is powerful and capable of expressing any exogenous gene on an industrial scale, and as a result, have found that an expression vector containing a chick β-actin gene promoter, when any exogenous gene is incorporated therein, can express said exogenous gene at an extremely higher level than the conventional promoter.

Furthermore, in order to develop a more powerful promoter and an expression vector containing the same, the present inventors have continuously studied as to an improvement of the chick β-actin gene promoter, and as a result, have succeded in constructing a novel hybrid promoter which has a still more powerful promoter activity. It has been found that this novel hybrid promoter can express an exogenous gene at an expression level several to about ten times higher than the natural chick β-actin gene promoter.

That is, the present invention provides an expression vector containing a chick β-actin gene promoter which can express an exogenous gene at an extremely high level in an expression system employing an animal cell.

BRIEF DESCRIPTION OF THE DRAWINGS

FIG. 1 shows a DNA sequence of a chick β-actin gene promoter;

FIG. 2 shows a DNA sequence recognized by the restriction enzyme NcoI;

FIG. 3 shows a DNA sequence after cleavage with the restriction enzyme NcoI;

FIG. 4 shows a position of HindIII linker incorporated at a downstream of a promoter in plasmid p28 constructed in Example 1;

FIG. 5 shows a DNA sequence of a hybrid promoter comprising a chick β-actin gene promoter and a rabbit β-globin gene, the hybrid promoter being contained in plasmid pAG-2 as constructed in Example;

DETAILED EXPLANATION OF THE INVENTION

Figure 6:
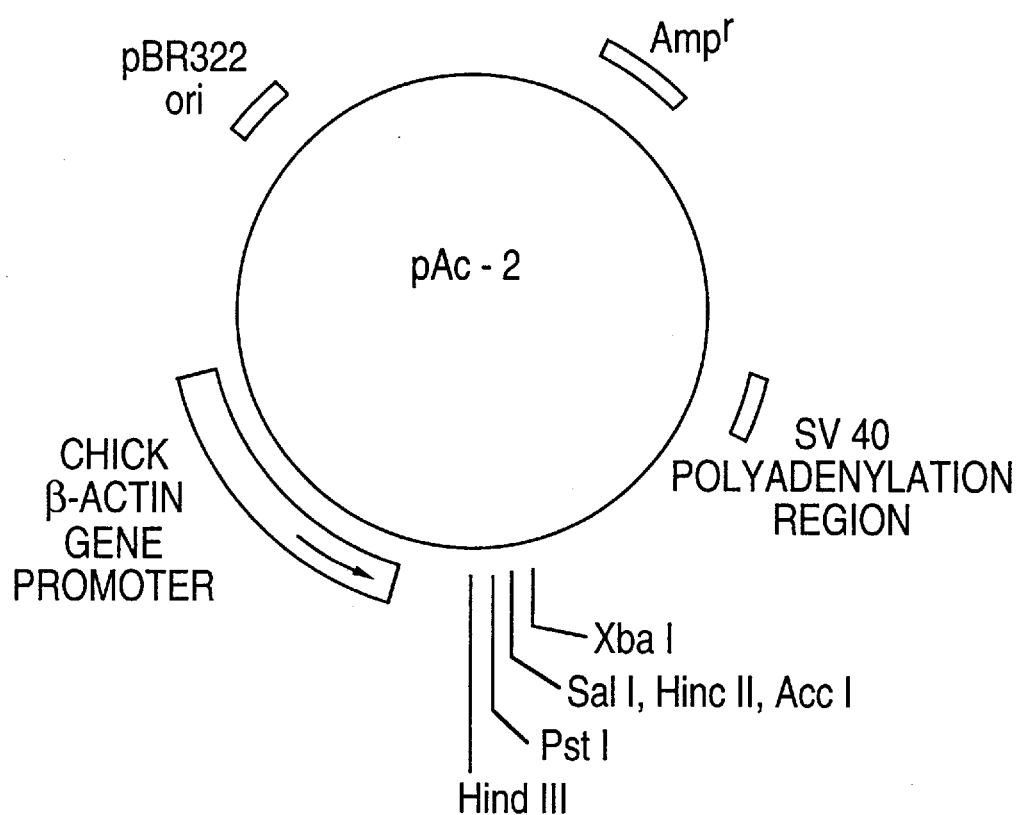
FIG. 6 shows the structure of plasmid pAc-2.

β-Actin is present in every cell and associated with a variety of cellular functions. It is one of major structural proteins ranging from protozoa to eucaryotes including human being and the amino acid sequences thereof are extremely homologous to each other.

In relation to an expression system using a β-actin gene promoter other than chick β-actin gene promoter, there has been known a process for preparing a protein using a vector containing a human β-actin gene promoter [P. Gunning et al., Proc. Natl. Acad. Sci. USA, 4831–4835 (1987)]. However, according to this report, the promoter activity is about 1.7 times higher than that of the SV 40 early gene promoter and this is still insufficient in practical viewpoint. In recent years, a promoter activity of the human β-actin gene promoter has been compared in various host cells [Gene 65, 135–139 (1988)]. This report shows that the human β-actin gene promoter demonstrated, in mouse-derived cells, a rather powerful activity than the SV 40 early promoter but, in human-derived cells or monkey-derived cells, a lower activity than the SV 40 early promoter.

On the contrary, the chick β-actin gene promoter of the present invention exhibits a promoter activity at least 5 to 10 times higher than that of the well known SV 40 early promoter and shows a powerful activity not only in mouse-derived cells (e.g. L cell) but also in hamster-derived cells (e.g. CHO cell), African green monkey-derived cells (e.g. COS cell) and the other animal cells.

The chick β-actin gene promoter used in the present invention is a gene fragment containing a DNA sequence of FIG. 1. A chick β-actin gene has already been cloned by T. A. Kost et al. [Nucleic Acids Research 11, No. 23, 8286–8287 (1983)].

The chick β-actin gene promoter used for an expression vector for expression of an exogenous gene of the present invention is a gene fragment having a high content of G (guanine) and C (cytosine) as a whole and containing sequences characteristic of a promoter such as TATA box [Ann. Res. Biochem., 50, 349–383 (1981)] and CCAAT box [Nucleic Acids Research 8, 127–142 (1980)].

In the DNA sequence of the promoter shown in FIG. 1, a DNA region from -909 G to -7 G is considered to be a region (intron) to be deleted (spliced) after transcription into messenger RNA.

According to a preferable embodiment of the present invention, there is used, as the chick β-actin gene promoter incorporated into a vector, a gene fragment 3' of which contains at least up to cytosine (C) at -5 position. It is generally known that a promoter activity is little affected by deletion of a part of the DNA sequence (e.g. up to about −30 bp) upstream of the initiation codon (ATG) of the original structural gene of β-actin. In case of the chick β-actin gene promoter, however, it was confirmed by the present inventors that the desired exogenous gene can be expressed at a higher level by using a promoter which contains base pairs up to cytosine (C), i.e. up to five base pairs upstream from the initiation codon (ATG) of the original structural gene of β-actin.

The modified β-actin gene promoter used in the present invention includes a hybrid promoter formed by incorporating a second promoter into an intron region of the above chick β-actin gene promoter. The hybrid promoter of the present invention is a novel promoter which can express an exogenous gene at an extremely high level showing a synergetic effect wherein the incorporated second promoter acts as an enhancer for the β-actin gene promoter while the β-actin gene promoter also acts as an enhancer for the incorporated second promoter. In the present specification, the second promoter means a promoter other than the chick β-actin gene promoter, which promoter functions in an animal cell. Preferably, a promoter derived from a virus infectious in an animal cell, and more preferably, the SV 40 early promoter, LTR of Rous sarcoma virus and the like are used for construction of the above hybrid promoter. Such hybrid promoter of the present invention shows a surprisingly powerful promoter activity, which activity is still several to 10 times higher than that of the chick β-actin gene promoter which itself has a powerful promoter activity.

The hybrid promoter as mentioned above can be prepared by incorporating the second promoter into the intron region of the chick β-actin gene promoter. In this case, the incorporation of the second promoter should be carried out in such a manner that the initiation codon (ATG) does not present in the DNA sequence ranging from the downstream (3') of the site into which the second promoter is incorporated to the splicing acceptor region. Most preferably, the second promoter is incorporated into MboII site in the chick β-actin gene promoter.

When the second promoter is incorporated into the intron region of the chick β-actin gene promoter as mentioned above, the incorporated chick β-actin gene promoter is preferably such that the 3' end thereof contains at least up to cytosine (C) at -5 position in FIG. 1.

The modified chick β-actin gene promoter of the present invention further includes a hybrid promoter which is constructed by deleting all genes from the middle of the intron region of the chick β-actin gene promoter to a location downstream (3') thereof including a splicing acceptor sequence, and linking thereto a gene containing another splicing acceptor sequence. Such an exogenous gene containing a splicing acceptor sequence includes, for example, a gene fragment containing a splicing acceptor sequence from a rabbit β-globin gene. In this way, by replacing the splicing acceptor sequence of the chick β-actin gene promoter with another splicing acceptor sequence, the promoter activity of the chick β-actin gene promoter can further be enhanced.

For linking a gene containing another splicing acceptor sequence to the promoter of the chick β-actin gene promoter, a gene from the middle of the intron region of the chick β-actin gene promoter to a location downstream thereof is deleted and thereto a gene containing another splicing acceptor sequence is linked. Such a deletion and a linking are preferably carried out at the MboII site as mentioned above.

An expression vector for expression in an animal cell of the present invention has such a characteristic structure that contains the above-mentioned chick β-actin gene promoter or modified promoter thereof and further contains a suitable restriction enzyme site downstream of said promoter where an exogenous gene can be incorporated. Such a restriction enzyme site may contain a recognition site of a single restriction enzyme or recognition sites of two or more restriction enzymes for facilitating an incorporation of various exogenous genes. In order to express the desired exogenous gene more efficiently, the expression vector of the present invention may further contain a polyadenylation sequence which is incorporated downstream of the site of incorporation of a structural gene to be expressed. For cloning a transformant cell, a suitable marker gene may also be incorporated into the vector.

The expression vector of the present invention may further contain a gene derived from E. coli for cloning in E. coli. Such gene derived from E. coli includes, for example, replication origin in E. coli, a suitable drug resistant gene which acts as a selection marker in cloning (e.g. a resistant gene to ampicilin, tetracycline, etc.). When a gene derived from the plasmid pBR322 is incorporated into the vector, it is preferred to delete a toxic sequence inhibiting a replication of the vector in a host cell which resides at around the replication origin (ori) of pBR322 [Nature 293, 79–81 (1981)].

When a cell producing a large T antigen of SV 40, for example, a COS cell (derived from African green monkey kidney) is employed as a host cell for expression of the desired exogenous gene, a replication origin which functions in an animal cell (e.g. SV 40 ori) may be further incorporated into the expression vector of the present invention, which enables an expression of an exogenous gene more efficiently. Examples of the preferable expression vector of the present invention employing the chick β-actin gene promoter are pAc-2 (FIG. 6) which can be used when a mouse L cell is used as the host cell and pSAc-2 (FIG. 7) which is effectively used when a COS cell is used as the host cell.

In order to enhance an expression efficiency of an exogenous gene, a dihydrofolate reductase (DHFR) gene may also be incorporated into the expression vector of the present invention, or alternatively, co-transfection may be conducted with a DHFR expression plasmid. In this case, a DHFR gene-defective cell is preferably employed as a host cell and an addition of methotrexate to a culture medium amplifies a gene in a transformant cell, which provides higher expression of the gene. Although such a method for enhancing an expression efficiency using a DHFR gene is already known, this can be applied to the expression vector of the present invention so that an expression efficiency is greatly improved.

Since β-actin is present in a variety of animal cells, the expression system of the present invention is applicable to a wide range of host cells with an extremely high expression efficiency, which is quite useful in industrial viewpoint.

The expression vector of the present invention can provide an extremely high expression level which hitherto has never been achieved, and is useful for the expression of an exogenous gene even in the industrial-scale production.

The present invention is more specifically illustrated by the following Examples wherein a β-galactosidase gene of E. coli and a hepatitis B surface antigen (HBs) gene are employed as an exogenous gene, but should not be construed to be limited thereto.

In Examples, phage, plasmid, DNA, various enzymes, E. coli, culture cell and the like were treated by the procedure described in the following texts and a magazine:

1. MOLECULAR CLONING A LABORATORY MANUAL ed. by T. MANIATIS et al. (1982), COLD SPRING HARBOR LABORATORY

2. METHODS IN ENZYMOLOGY 65, ed. by L. GROSSMAN et al. (1980), ACADEMIC PRESS

3. DNA cloning ed. by D. M. Glover et al. (1985) IRL. PRESS

In Examples, the following abbreviations are employed.

CAT: Chloramphenicol acetyl transferase lacZ: β-Galactosidase (β-gal) structural gene

EXAMPLE 1

(Construction of expression vectors, pAc-2 and pSAc-2)

(1) Preparation of a promoter region of a chick β-actin gene promoter:

A plasmid pAZ1037 which contains a first exon, a first intron and a part of a second exon of a chick β-actin gene promoter and a CAT gene linked thereto [Nature 314, 286–289 (1985)] was digested with restriction enzyme NcoI (NEB #193). The restriction enzyme NcoI recognizes a sequence of six base pairs as shown in FIG. 2 and cleaves the sequence to form a sequence with 5' overhanging as shown in FIG. 3. In the present invention, the following procedures were carried out so that the splicing region between the first intron and the second exon of the chick β-actin gene promoter correctly functions when used as the expression vector.

That is, the NcoI-digested DNA was treated with S1 nuclease (Takara #2410A) to delete the 5' overhanging region and only one base pair adjacent thereto. In this reaction, a sample DNA (10 μg) was treated with 150 units of S1 nuclease in a solution (80 μl) of 30 mM sodium acetate, pH 4.6, 100 mM NaCl, 1 mM ZnSO$_4$ at 37° C. for 1 to 4 minutes.

After treating the DNA with S1 nuclease, the treated DNA was further treated with T4 DNA polymerase (Takara #2040A) to modify the single strand moiety of the DNA and thereto was linked a synthesized DNA pCCAAGCTTGG 5' end of which is phosphorylated (pHindIII linker, NEB #1050) with T4 DNA ligase (Takara #2011A) to cyclize. E. coli HB101 strain was transformed with the obtained DNA solution. After separating a single colony, a plasmid DNA in the transformed cells was collected and digested with restriction enzymes HindIII (NEB #104) and NarI (NEB #191). 6% Acrylamide gel electrophoresis was conducted and a clone was selected which contained a DNA fragment with a suitable size. The DNA fragment was cloned into the SalI-KpnI site of phage vector M13mp19 (NEB #400-19) and a DNA sequence about the HindIII site was determined by a dideoxy method [Proc. N.A.S. 74, 5463–5477 (1977)] to screen the desired clone.

The thus obtained plasmid clone p28, as shown in FIG. 4, retained a DNA sequence ranging from the splicing region to the structural gene of the natural chick β-actin gene and had a structure where a gene at 3' end from the initiation codon (ATG) was deleted and thereto HindIII site was incorporated. Following the same procedure, clone p29, where up to 2 base pairs upstream the ATG were deleted, and clone p3, where up to 20 base pairs upstream the ATG were deleted, were also obtained.

(2) Construction of expression vector, pAc-2:

A plasmid pSV2-cat containing a splicing region for SV 40 early transcription and a polyadenylation signal [Molecular Cell Biology 2, 1044–1051 (1982)] was digested with restriction enzyme MflI (Takara #1070A). The cleaved sites were modified with T4 DNA polymerase and thereto was linked a phosphorylated HindIII linker with T4 DNA ligase. The obtained plasmid was further digested with restriction enzymes HindIII and BamHI (NEB #136) and the cleaved fragments were subjected to 6% acrylamide gel electrophoresis to extract a HindIII-BamHI fragment of about 900 bp. The plasmid p28 constructed in the above procedure (1) was digested with restriction enzymes HindIII and BamHI and dephosphorylated with alkaline phosphatase derived from calf intestine (Takara #2250A). This was linked to the above HindIII-BamHI fragment of about 900 bp with T4 DNA ligase to cyclize to give a plasmid pAc-2 (FIG. 6).

(3) Construction of an expression vector, pSAc-2:

The same plasmid pSV2-cat as used in the above procedure (2) was digested with restriction enzymes AccI (NEB #161) and SphI (NEB #182) and the cleaved sites were blunt-ended with T4 DNA polymerase. This was linked and cyclized in the presence of a phosphorylated XbaI linker (NEB #1032) with T4 DNA ligase to prepare a plasmid pSV-cat-de1E [Proc. Natl. Acad. Sci. USA 83, 9537–9541 (1986)].

Figure 7:
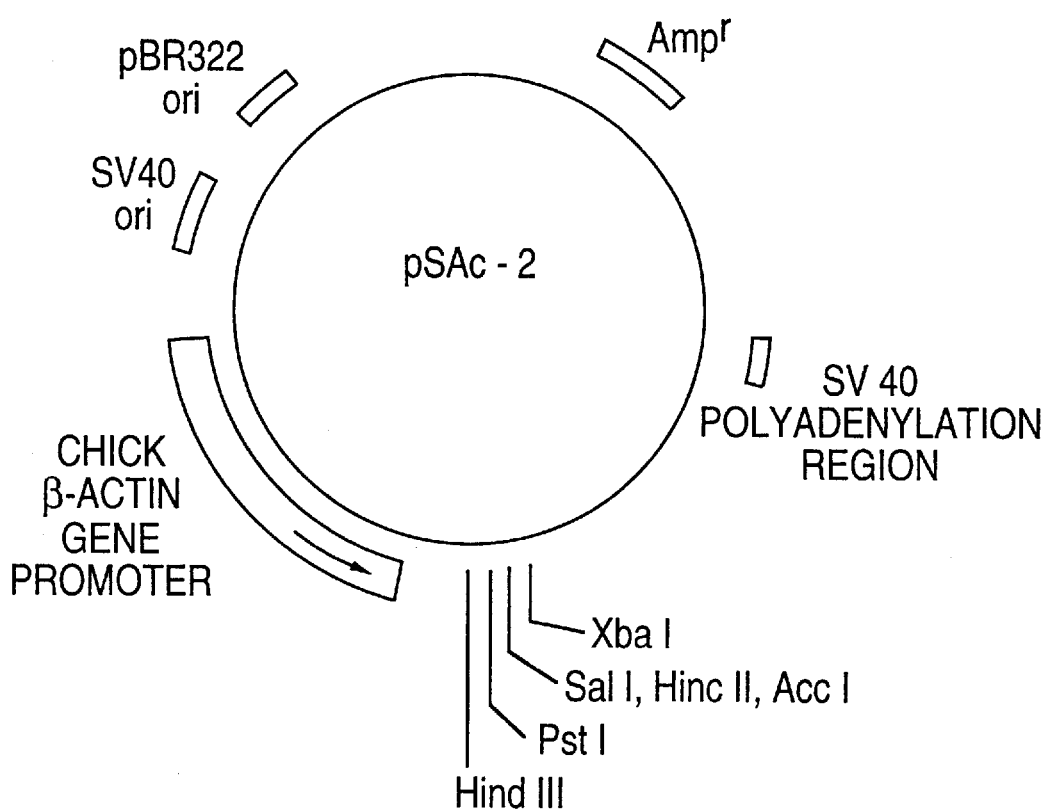
FIG. 7 shows the structure of plasmid pSAc-2.

This plasmid pSV-cat-de1E was digested with restriction enzyme HindIII and the cleaved sites were modified with T4 DNA polymerase. This was linked and cyclized in the presence of a phosphorylated XhoI linker (NEB #1030) with T4 DNA ligase. The obtained plasmid was further digested with restriction enzymes EcoRI (NEB #101) and XhoI (NEB #146) and the cleaved fragments were subjected to 1% agarose gel electrophoresis to extract an EcoRI-XhoI fragment of about 2 kbp. The plasmid pAc-2 constructed in the above procedure (2) was digested with restriction enzymes XhoI and EcoRI to give an XhoI-EcoRI fragment of about 2.2 kbp, to which was linked the above EcoRI-XhoI fragment of about 2 kbp to cyclize to prepare a plasmid pSAc-2 (FIG. 7).

EXAMPLE 2

(Construction of β-galactosidase expression plasmids pAc-lacZ and pSAc-lacZ)

(1) Preparation of a β-galactosidase gene fragment:

A plasmid pCH110 [Pharmacia #27-4508-01], which contained whole lacZ gene encoding β-galactosidase, was digested with restriction enzymes HindIII and BamHI and the cleaved fragments were subjected to 1% agarose gel electrophoresis to prepare a HindIII-BamHI fragment of about 3.8 kbp. This fragment contained a splicing region and a polyadenylation region of SV 40 early gene transcript.

(2) Construction of plasmid pAc-2:

The plasmid p28 constructed in Example 1 (1) was digested with restriction enzymes HindIII and BamHI and the cleaved sites were dephosphorylated with alkaline phosphatase derived from calf intestine. To this was linked the HindIII-BamHI fragment of about 3.8 kbp obtained in the above procedure (1) to construct a plasmid pAc-lacZ.

Following the same procedure, plasmids pAc-lacZ(29) and pAc-lacZ(3) were constructed from the plasmids p29 and p3 obtained in Example 1 (1), respectively.

(3) Construction of pSAc-lacZ:

The plasmid pSAc-2 constructed in Example 1 (3) was digested with restriction enzymes HindIII and BamHI and the cleaved sites were dephosphorylated with alkaline phosphatase derived from calf intestine. To this was linked the HindIII-BamHI fragment of about 3.8 kbp obtained in the above procedure (1) with T4 DNA ligase to cyclize to construct a plasmid pSAc-lacZ.

EXAMPLE 3

(Construction of Hapatitis B surface antigen (HBsAg) expression vector pSAc-HBs)

A plasmid pAS101 containing a repressible acid phosphatase promoter and being capable of producing HBsAg after transformation of yeast (Japanese Patent Second Publication No. 55951/1984) was digested with restriction enzyme XhoI and the cleaved fragments were subjected to 6% acrylamide gel electrophoresis to extract a DNA fragment containing HBsAg gene of about 1.3 kbp.

On the other hand, the plasmid pSAc-2 constructed in Example 1 (3) was digested with restriction enzyme SalI (Takara #1080A) and the cleaved sites were dephosphorylated with alkaline phosphatase derived from calf intestine. This was linked to the above DNA fragment of about 1.3 kbp containing HBsAg gene with T4 DNA ligase to cyclize and prepare an HBsAg expression plasmid pSAc-HBs.

Next, a control expression plasmid pSVE-HBs was constructed for evaluation of an expression of HBsAg in the following procedure.

The above plasmid pAS101 (10 µg) was reacted with restriction enzyme XhoI (10 U) at 37° C. for 4 hours and the obtained fragments were subjected to 0.75% agarose gel electrophoresis. 1.3 Kb band containing an HBsAg gene was separated from the agarose gel and put in a dialysis tube, which was again subjected to an electrophoresis. After elution of DNA from the gel fragment, only a DNA solution was taken out from the dialysis tube and DNA was extracted by an ethanol precipitation. The extracted DNA fragment containing HBsAg gene (1 µg) was reacted with T4 DNA polymerase (1 U) at 37° C. for 30 minutes. Treatment with phenol and ethanol precipitation were conducted to extract DNA.

On the other hand, a plasmid pKSV-10 containing an SV 40 early gene promoter (Pharmacia #27-4926-01) (1 µg) was reacted with restriction enzyme BglII (1 U) at 37° C. for 1 hour. DNA was extracted by phenol treatment and ethanol precipitation. The extracted DNA was treated with T4 DNA polymerase in the same manner as mentioned above. A mixture of the HBsAg gene fragment which was blunt-ended with T4 DNA polymerase reaction (500 ng) and pKSV-10 (50 ng) was reacted in the presence of T4 DNA ligase (1 U) at 4° C. for 12 hours. E. coli HB101 was transformed with this reaction mixture. A plasmid was extracted from the transformant to give a plasmid pSVE-HBs where the HBsAg gene was incorporated into pKSV-10.

EXAMPLE 4

(Production of β-galactosidase in COS cell and L-cell)

COS cells or L-cells were plated on 100 mm round Petri dish at 1×10⁶ cells/dish and each 20 µg of the following plasmids DNA was introduced into these host cells by a calcium phosphate method in accordance with the conventional procedure.

The cells were contacted with calcium phosphate-gel for 24 hours and further cultured in a 10% FCS-DME for 24 hours. The cells were peeled off the dish with trypsin treatment and pelleted by a low-speed centrifugation. The pellet was suspended in F-T buffer (250 mM sucrose, 10 mM Tris-HCl, pH 7.5, 10 mM EDTA) (200 µl) and a freezing-thawing procedure was repeated for three times, followed by centrifugation to collect a supernatant.

Using 10 µl of the thus obtained cell extract (200 µl), a β-gal activity was measured. The measurement of β-gal activity was conducted by detecting a change in absorbance at 420 nm accompanied with a color development of ONPG (o-nitrophenyl-β-D-galactopyranoside) in the conventional manner. Table 1 shows a relative value where the absorbance shown by the cell extract of COS-cells or L-cells transformed with the plasmid pCH110 containing an SV 40 early promoter [Pharmacia #27-4508-01] was made 1.

TABLE 1

| | β-Gal Activity | |
|---|---|---|
| Plasmid | COS-cell | L-cell |
| (1) pCH110 | 1.0 | 1.0 |
| (2) pAc-lacZ | 4.0 | 5.0 |
| (3) pAc-lacZ(3) | 1.2 | — |
| (4) pAc-lacZ(29) | 2.7 | — |
| (5) pSAc-lacZ | 57.2 | 3.0 |
| (6) pSAc-2 | 0.01 | 0.01 |

As shown in table 1, the plasmids pAc-lacZ and pSAc-lacZ, which contained the chick β-actin gene promoter, showed 3 to 5 times higher value in L-cell than the plasmid pCH110 which contained the SV 40 early gene promoter. Since the SV 40 ori functioned effectively, the plasmid pSAc-lacZ showed more than 50 times higher value in COS-cell than the plasmid pCH110.

EXAMPLE 5

(Production of HBsAg in COS-cell)

COS-cells (1×10⁵ cells/well) were plated on a Falcon 6-well plate for cell culture and, in accordance with the conventional DEAE-Dextran method, the following plasmid DNAs (each 5 µg) were introduced into the cells. Three days after introduction of DNA, the culture supernatant three days after introduction of DNA was collected with CellPhect Transfection Kit (Pharmacia) and an HBsAg activity was measured with HBsAg detection kit "Auslia II" (manufactured by Dainabbott). The results are shown in Table 2.

As shown in table 2, the plasmid pSAc-HBs, which contained the chick β-actin gene promoter, showed 3 to 5 times higher value than the plasmid pSVE-HBs which contained the SV 40 early gene promoter.

TABLE 2

| Plasmid | HBsAg Activity (cpm) |
|---|---|
| (1) pSVE-HBs | 1,100 |
| (2) pSAc-HBs | 6,800 |
| (3) pSAc-2 | 300 |

EXAMPLE 6

(Preparation of expression vector containing hybrid promoter of the chick β-actin gene promoter and the SV 40 early promoter; pSA-lacZ and pAS-2)

The plasmid pSV2-cat used in Example 1 (2) was digested with restriction enzymes PvuII (Takara #1076A) and HindIII and the cleaved fragments were subjected to 6% acrylamide gel electrophoresis to prepare a PvuII-HindIII fragment of about 340 bp containing the SV 40 early promoter. The PvuII-HindIII fragment was modified with T4 DNA polymerase at its termini and thereto was linked a phosphorylated XbaI linker with T4 DNA ligase. After digesting the ligate with restriction enzyme XbaI (Takara #1093A), the cleaved fragments were subjected to 6% acrylamide gel electrophoresis to prepare a XbaI-XbaI fragment of about 350 bp.

The plasmid pSAc-2 constructed in Example 1 (3) was digested with restriction enzymes XbaI and PstI and the cleaved fragments were subjected to 1% agarose gel electrophoresis to prepare a XbaI-PstI fragment of about 1.6 kbp. This fragment was digested with restriction enzyme MboII (NEB #148) and the cleaved sites were modified with T4 DNA polymerase and thereto was linked a phosphorylated XbaI linker with T4 DNA ligase. The ligate was digested with restriction enzymes XhoI and HindIII and the cleaved fragments were subjected to 1% agarose gel electrophoresis to prepare a XhoI-HindIII fragment of about 1.3 kbp.

The plasmid pAc-lacZ constructed in Example 2 was digested with restriction enzymes XhoI and HindIII and the cleaved fragments were subjected to 1% agarose gel electrophoresis to prepare a XhoI-HindIII fragment of about 5.8 kbp. This fragment was mixed with the above XhoI-HindIII fragment of about 1.3 kbp and, after digestion with restriction enzyme XbaI, ligated to each other with T4 DNA ligase to cyclize and construct a plasmid pAc-lacZ-XbaI.

This plasmid pAc-lacZ-XbaI was digested with restriction enzyme XbaI and thereto was linked the above XbaI-XbaI fragment of about 350 bp with T4 DNA ligase to construct a plasmid pAS-lacZ.

The plasmid pAc-2 constructed in Example 1 (2) was digested with restriction enzymes HindIII and BamHI and the cleaved fragments were subjected to 1% agarose gel electrophoresis to extract a HindIII-BamHI fragment of about 900 bp, which contained the splicing region and the polyadenylation signal of the SV 40 early promoter.

Figure 8:
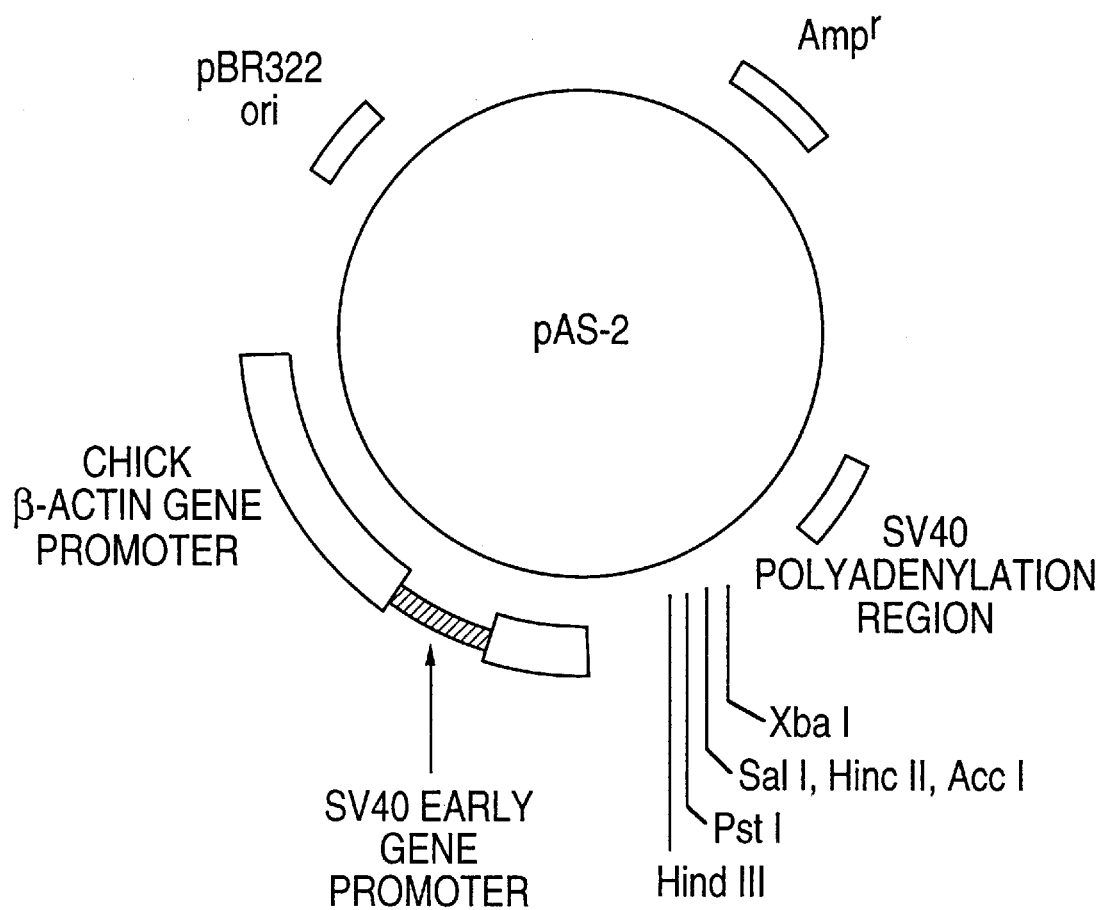
FIG. 8 shows the structure of plasmid pAS-2.

The plasmid pAS-lacZ was digested with restriction enzymes HindIII and BamHI and the cleaved fragments were subjected to 1% agarose gel electrophoresis to prepare a HindIII-BamHI fragment of about 3.7 kbp. To this HindIII-BamHI fragment of about 3.7 kbp was linked the above HindIII-BamHI fragment of about 900 bp with T4 DNA ligase to construct a plasmid pAS-2 (FIG. 8).

EXAMPLE 7

(Preparation of expression vector containing hybrid promoter of the chick β-actin gene promoter and the RSV-LTR promoter; pAR-lacZ and pAR-2)

A plasmid pRSV-cat containing LTR of RSV [Proc. Natl. Acad. Sci. USA. 79, 6777–6781 (1982)] was digested with restriction enzymes NruI (NEB #192) and TaqI (NEB #149) and the cleaved fragments were subjected to 6% acrylamide gel electrophoresis to prepare a NruI-TaqI fragment of about 340 bp. This NruI-TaqI fragment was modified with T4 DNA polymerase at its termini and thereto was linked a phosphorylated XbaI linker. After digesting the ligate with restriction enzyme XbaI, the cleaved fragment was subjected to 6% acrylamide gel electrophoresis to prepare a XbaI-XbaI fragment of about 350 bp.

The plasmid pAc-lacZ-XbaI constructed in Example 6 was digested with restriction enzyme XbaI and thereto was linked the above XbaI-XbaI fragment of about 350 bp with T4 DNA ligase to construct a plasmid pAR-lacZ.

Figure 9:
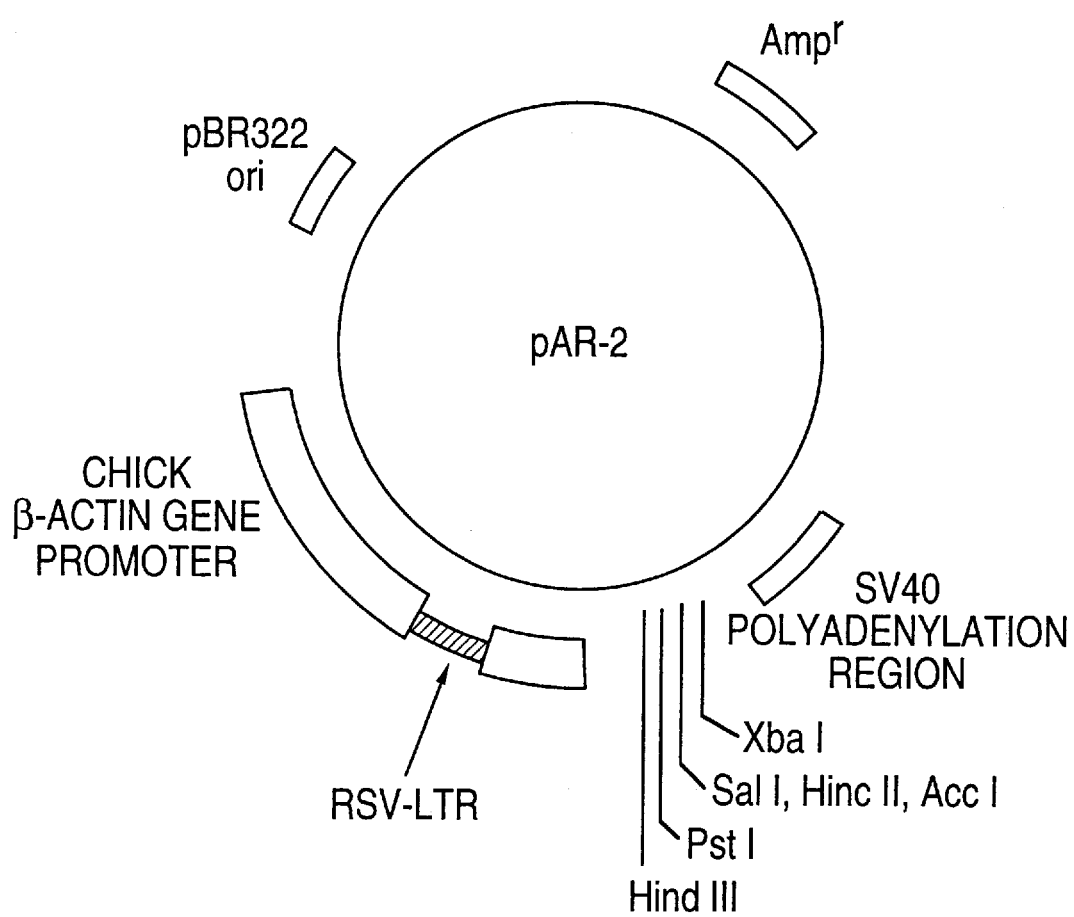
FIG. 9 shows the structure of plasmid pAR-2.

The plasmid pAR-lacZ was digested with restriction enzymes HindIII and BamHI and the cleaved fragments were subjected to 1% agarose gel electrophoresis to prepare a HindIII-BamHI fragment of about 3.7 kbp. To this HindIII-BamHI fragment of about 3.7 kbp was linked the HindIII-BamHI fragment of about 900 bp prepared in Example 6 with T4 DNA ligase to construct a plasmid pAR-2 (FIG. 9).

EXAMPLE 8

(Preparation expression vector containing hybrid promoter of the chick β-actin gene promoter and the rabbit β-globin gene; pAG-lacZ and pAG-2)

Figure 10:
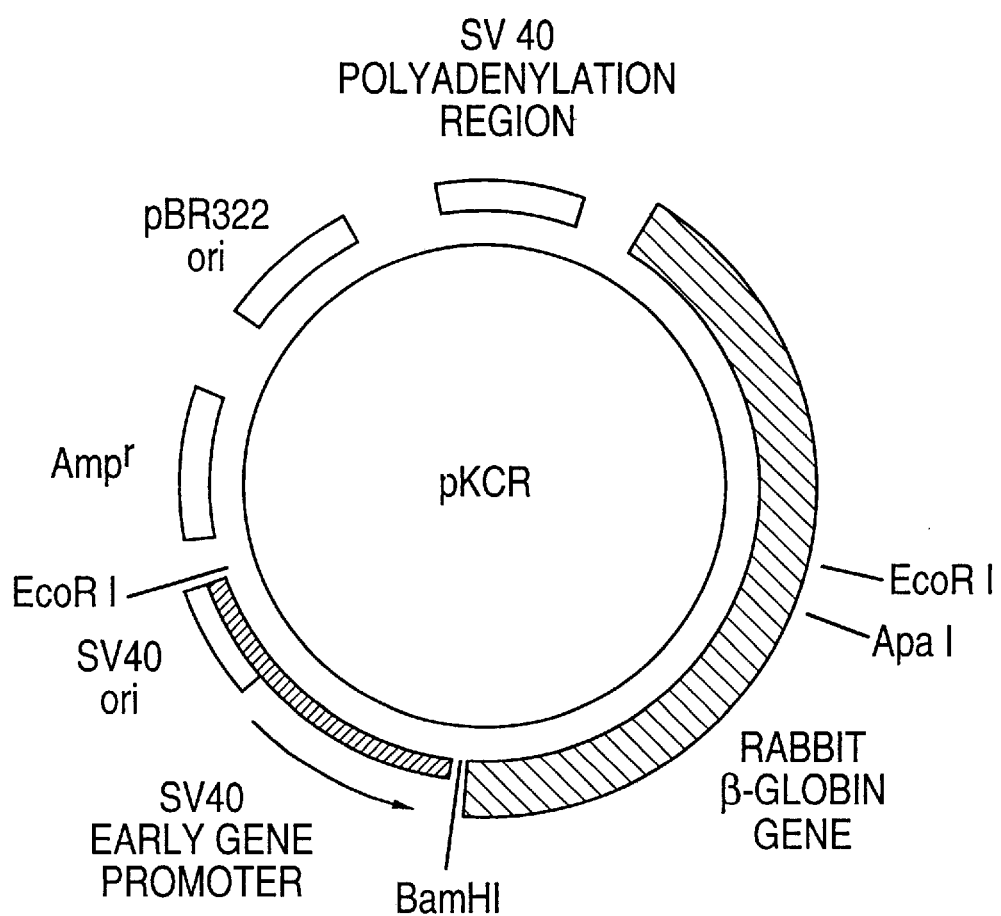
FIG. 10 shows the structure of plasmid PKCR.

A plasmid pKCR containing a rabbit β-globin gene from the middle of the second exon to the middle of the third exon thereof [Proc. Natl. Acad. Sci. USA. 78, 1527–1531 (1981)] (FIG. 10) was digested with restriction enzyme ApaI (NEB #ApaI) and the cleaved sites were modified with T4 DNA polymerase and thereto was linked a phosphorylated XbaI linker with T4 DNA ligase. This ligate was digested with restriction enzyme EcoRI and the cleaved sites were modified with DNA polymerase I Large Fragment (NEB #210). Thereto was linked a pHindIII linker (NEB #1022) with T4 DNA ligase and the ligate was digested with restriction enzymes XbaI and HindIII, followed by 6% acrylamide gel electrophoresis to prepare a XbaI-HindIII fragment of about 90 bp which contained a splicing acceptor site in the second intron of the rabbit β-globin gene.

The plasmid pAc-lacZ-XbaI constructed in Example 6 was digested with restriction enzymes XbaI and HindIII and the cleaved fragments were subjected to 1% agarose gel electrophoresis to prepare a XbaI-HindIII fragment of about 7 kbp. Thereto was linked the above XbaI-HindIII fragment of about 90 bp with T4 DNA ligase to construct a plasmid pAG-lacZ.

Figure 11:
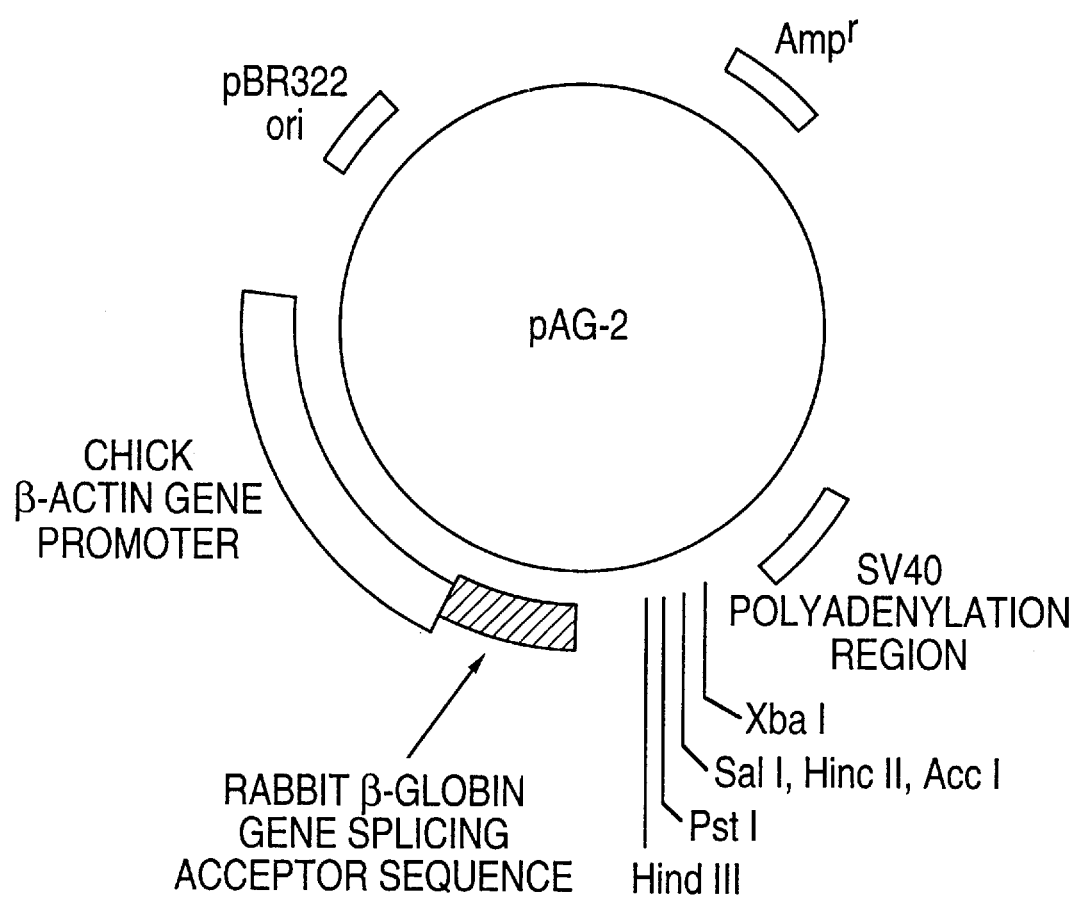
FIG. 11 shows the structure of plasmid pAG-2.

This plasmid pAG-lacZ was digested with restriction enzymes HindIII and BamHI and the cleaved fragments were subjected to 1% agarose gel electrophoresis to prepare a HindIII-BamHI fragment of about 3.3 kbp. To this HindIII-BamHI fragment of about 3.3 kbp was linked the above-prepared HindIII-BamHI fragment of about 900 bp with T4 DNA ligase to construct a plasmid pAG-2 (FIG. 11).

EXAMPLE 9

(Construction of expression vector containing SV 40 ori; pAcS-lacZ, pAcS-2, pARS-lacZ, pARS-2, pAGS-lacZ and pAGS-2)

Figure 12:
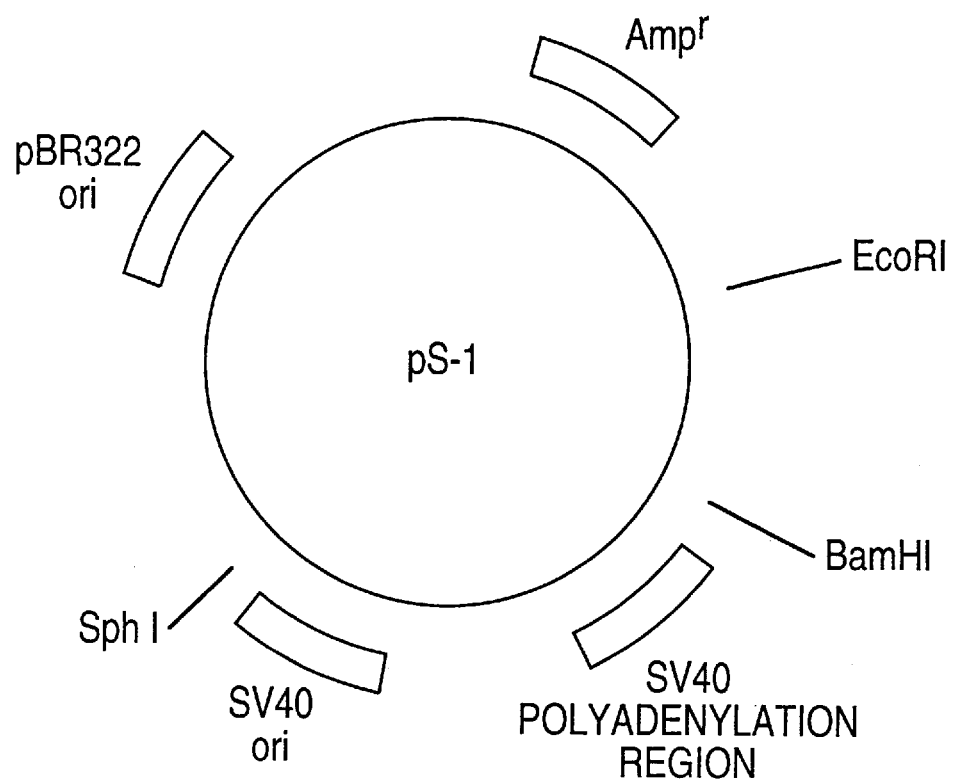
FIG. 12 shows the structure of plasmid pS-1.

The plasmid pSV2-cat used in Example 1 (2) was digested with restriction enzymes HpaI (NEB #105) and HindIII and the cleaved sites were modified with T4 DNA polymerase and ligated to each other with T4 DNA ligase to cyclize and prepare a plasmid pS-1 (FIG. 12).

Figure 13:
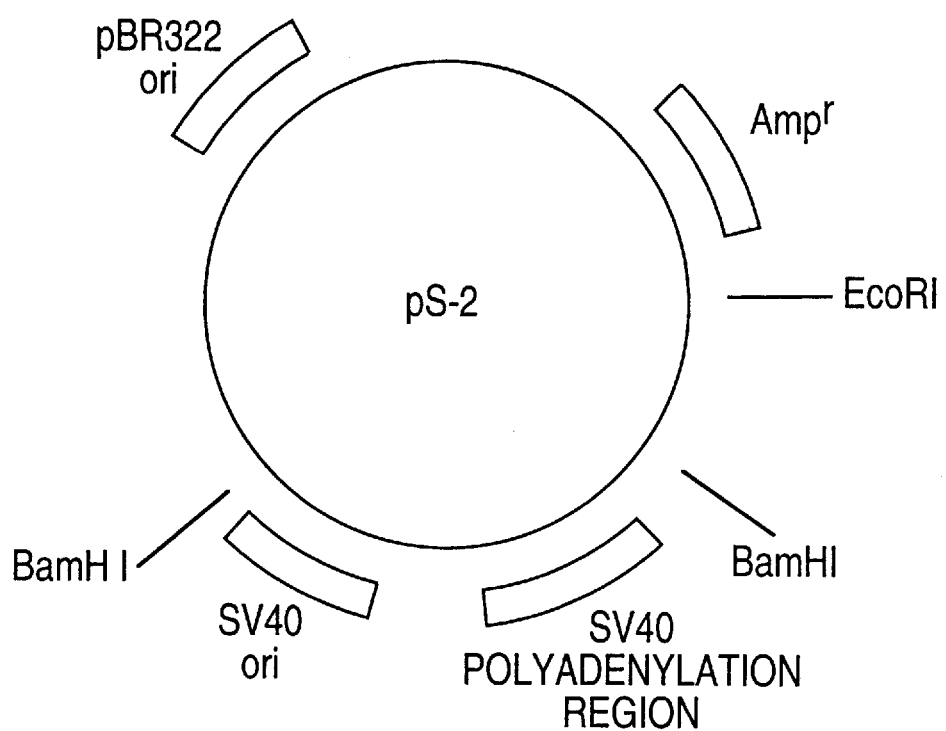
FIG. 13 shows the structure of plasmid pS-2.

This plasmid pS-1 was digested with restriction enzyme SphI and the cleaved sites were modified with T4 DNA polymerase and thereto was linked a phosphorylated BamHI linker (NEB #1021) with T4 DNA ligase to cyclize and prepare a plasmid pS-2 (FIG. 13).

This plasmid pS-2 was digested with restriction enzyme BamHI and the cleaved fragments were subjected to 6% acrylamide gel electrophoresis to give a BamHI-BamHI fragment of about 350 bp which contained a polyadenylation signal of SV 40 early transcription.

The plasmid pAc-lacZ constructed in Example 2 was digested with restriction enzyme BamHI and thereto was linked the above BamHI-BamHI fragment of about 350 bp with T4 DNA ligase to cyclize and construct a plasmid pAcS-lacZ.

Figure 14:
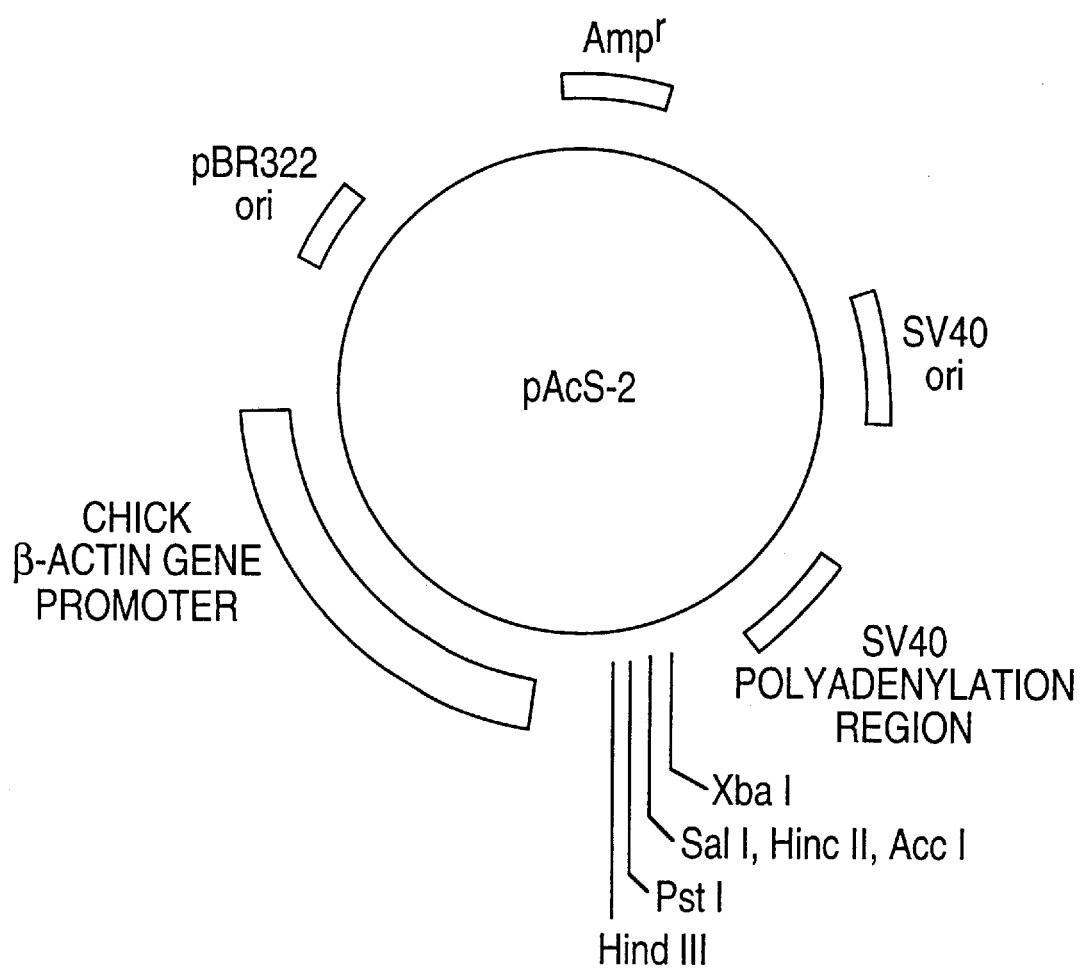
FIG. 14 shows the structure of plasmid pAcS-2.

The plasmid pAc-2 constructed in Example 1 (2) was digested with restriction enzyme BamHI and thereto was linked the above BamHI-BamHI fragment of about 350 bp with T4 DNA ligase to cyclize and construct a plasmid pAcS-2 (FIG. 14).

The plasmid pAR-lacZ constructed in Example 7 was digested with restriction enzyme BamHI and thereto was linked the above BamHI-BamHI fragment of about 350 bp with T4 DNA ligase to cyclize and construct a plasmid pARS-lacZ.

Figure 15:
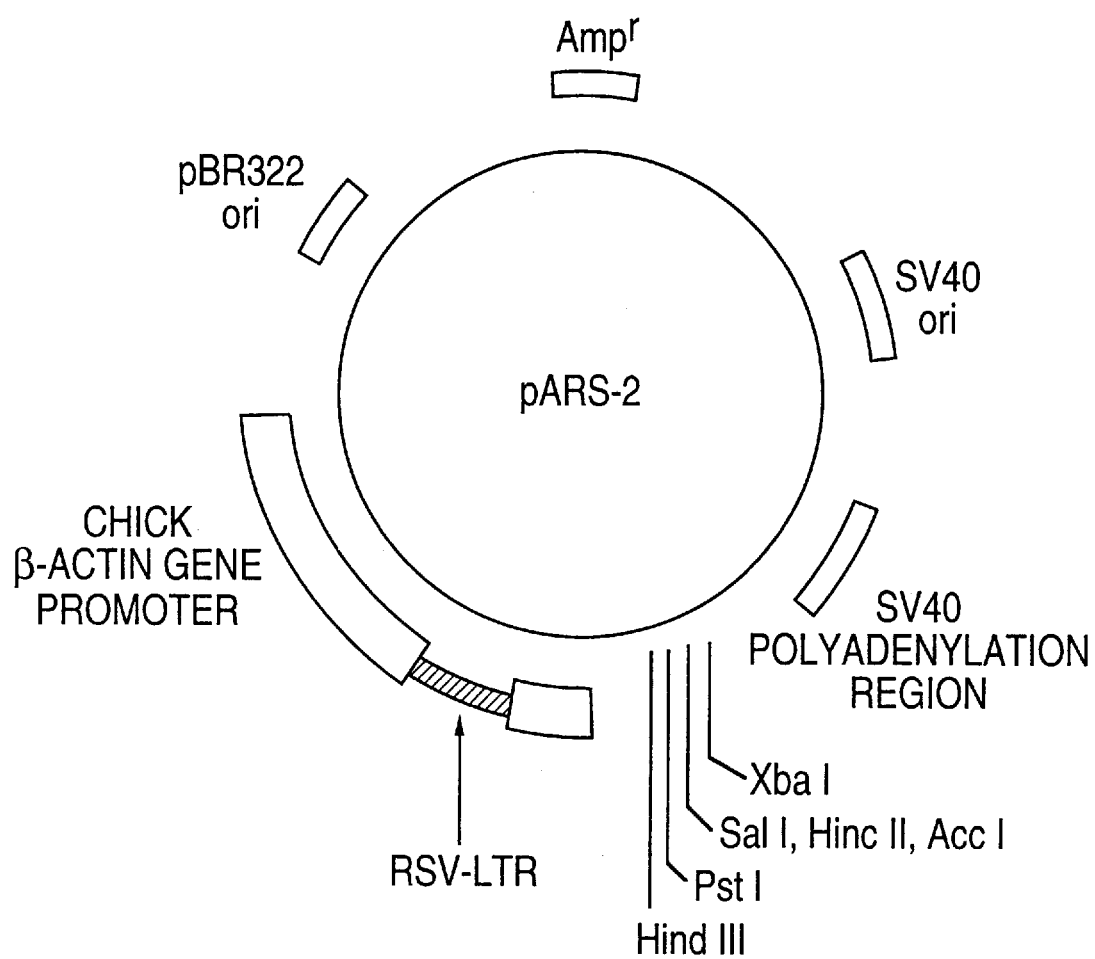
FIG. 15 shows the structure of plasmid pARS-2.
Figure 16:
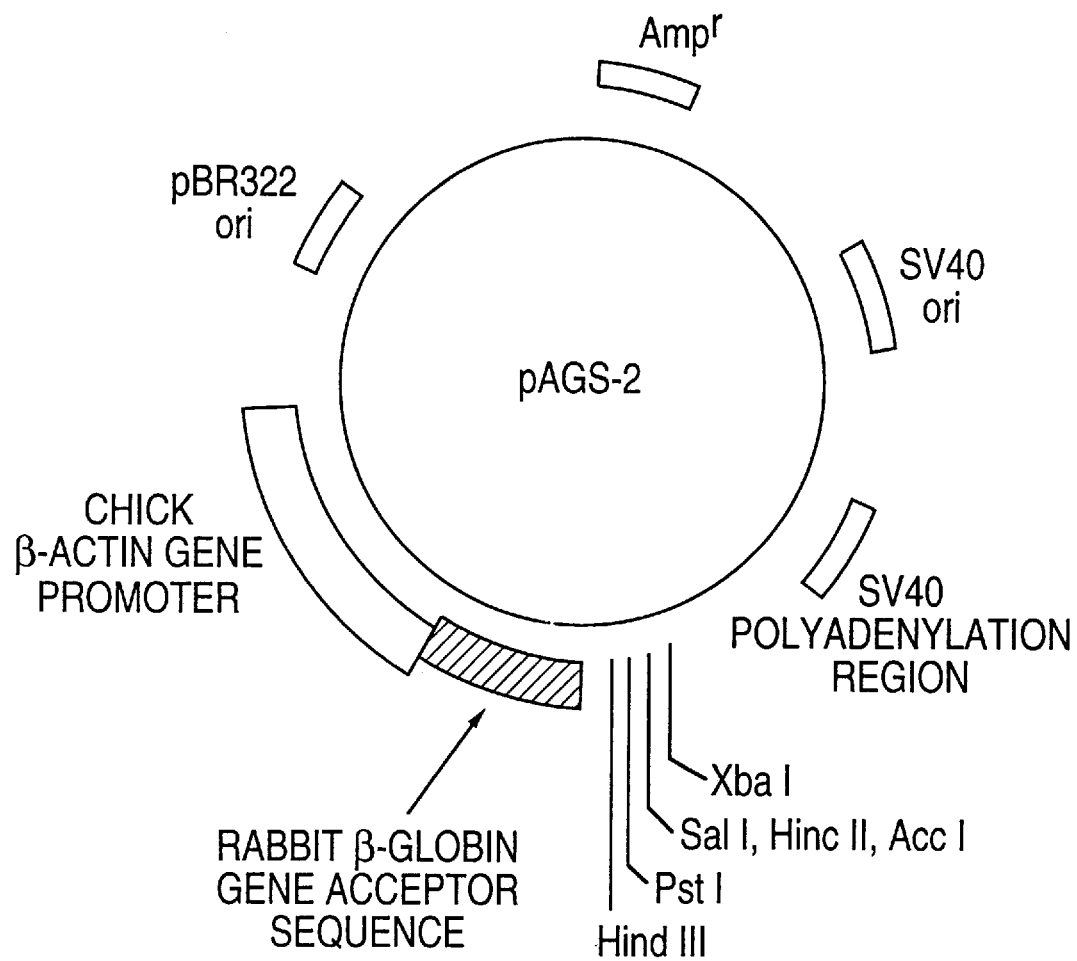
FIG. 16 shows the structure of plasmid pAGS-2.

In the same manner as mentioned above, there were constructed a plasmid pARS-2 (FIG. 15) from the plasmid pAR-2 constructed in Example 7, a plasmid pAGS-lacZ from the plasmid pAG-lacZ constructed in Example 8, and a plasmid pAGS-2 (FIG. 16) from the plasmid pAG-2 constructed in Example 8, respectively.

EXAMPLE 10

(Production of β-galactosidase with expression vector containing modified chick β-actin gene promoter)

COS cells or L-cells were plated on 100 mm round Petri dish at 1×10$^6$ cells/dish and each 20 µg of the various plasmids (pCH110, pAS-lacZ, pAR-lacZ, pAG-lacZ, pAcS-lacZ, pARS-lacZ, pAGS-lacZ) DNA was introduced into these host cells by a calcium phosphate method in accordance with the conventional procedure.

The cells were contacted with calcium phosphate-gel for 24 hours and further cultured in a 10% FCS-DME for 24 hours. The cells were peeled off the dish with trypsin treatment and pelleted by a low-speed centrifugation. The pellet was suspended in F-T buffer (250 mM sucrose, 10 mM Tris-HCl, pH 7.5, 10 mM EDTA) (200 µl) and a freezing-thawing procedure was repeated for three times, followed by centrifugation to collect a supernatant.

Using 10 µl of the thus obtained cell extract (200 µl), a β-gal activity was measured. The measurement of β-gal activity was conducted by detecting a change in absorbance at 420 nm accompanied with a color development of ONPG (o-nitrophenyl-β-D-galactopyranoside) in the conventional manner. Table 3 shows a relative value where the absorbance shown by the cell extract of COS-cells or L-cells transformed with the plasmid pCH110 containing an SV 40 early promoter [Pharmacia #27-4508-01] was made 1.

TABLE 3

| Plasmid | β-Gal Activity | |
|---|---|---|
| | COS-cell | L-cell |
| (1) pCH110 | 1.0 | 1.0 |
| (2) pAS-lacZ | 20.9 | 19.4 |
| (3) pAR-lacZ | 11.5 | 17.0 |
| (4) pAG-lacZ | 12.0 | 10.2 |
| (5) pAcS-lacZ | 15.0 | 4.5 |
| (6) pARS-lacZ | 55.8 | 23.9 |
| (7) pAGS-lacZ | 55.8 | 7.4 |
| pAc-lacZ-XbaI | 4.0 | 5.0 |
| pAc-lacZ | 4.0 | 5.0 |

As is clearly shown in Table 3, the plasmid where the lacZ gene was incorporated into the expression vector containing the hybrid promoter of the present invention showed an extremely high expression as compared with the expression plasmid (pAc-lacZ) containing the natural chick β-actin gene promoter.

EXAMPLE 11

(Production of HBsAg with expression vector containing the modified chick β-actin gene promoter)

(1) Construction of HBsAg-expression plasmids pAS-HBs, pAG-HBs, pAcS-HBs, pARS-HBs and pAGS-HBs:

The plasmid pAS101 (10 µg) used in Example 3 was reacted with restriction enzyme XhoI (10 U) at 37° C. for 4 hours and the cleaved fragments were subjected to 6% agarose gel electrophoresis. 1.3 Kb band containing HBs gene was cut off the agarose gel and put in a dialysis tube and further subjected to an electrophoresis. After DNA was eluted from the gel fragment, only a DNA solution was taken from the dialysis tube and DNA was extracted by an ethanol precipitation. The extracted DNA fragments (1 µg) containing HBsAg gene were reacted with T4 DNA polymerase (1 U) at 37° C. for 30 minutes. Then, phenol treatment and ethanol precipitation were conducted to extract DNA.

Next, six kinds of the plasmids constructed in Examples 6 to 9 (pAS-2, pAR-2, pAG-2, pAcS-2, pARS-2 and pAGS-2) were digested with restriction enzyme SalI and the cleaved fragments were dephosphorylated with alkaline phosphatase derived from calf intestine. Thereto was linked the above DNA fragment of about 1.3 kbp containing HBsAg gene with T4 DNA ligase to cyclize and construct an HBsAg-expression plasmids pAS-HBs, pAR-HBs, pAG-HBs, pAcS-HBs, pARS-HBs and pAGS-HBs, respectively.

As a reference expression plasmid for evaluation of HBsAg expression, the plasmid pSVES-HBs constructed in Example 3 was used.

(2) Expression of HBs in COS-cells:

COS-cells were plated on a Falcon 6-well plate for cell culture at 1×10$^5$ cells/well and, in accordance with the conventional procedure, each 5 µg of the following plasmid DNAs was introduced into the cells by an DEAE-Dextran method. Three days after introduction of DNA, a culture supernatant was separated with CellPhect Transfection Kit (Pharmacia) and an HBsAg activity was measured with HBsAg detection kit "Auslia II" (manufactured by Dainabbott). The results are shown in Table 4.

TABLE 4

| Plasmid | HBsAg Activity (cpm) |
|---------|----------------------|
| (1) pAS-HBs | 5100 |
| (2) pAR-HBs | 3000 |
| (3) pAG-HBs | 3100 |
| (4) pAcS-HBs | 3500 |
| (5) pARS-HBs | 6200 |
| (6) pAGS-HBs | 7200 |
| (7) pSVE-HBs | 1050 |

As shown in Table 4, the expression plasmids containing the modified chick β-actin gene promoter showed an HBsAg activity higher than those of the plasmid pSVE-HBs containing the SV 40 early gene promoter.

What is claimed is:

1. An expression vector for the expression of an exogenous gene in an animal cell, wherein said vector comprises a modified chick β-actin gene promoter and a restriction enzyme site for incorporating an exogenous gene downstream of said chick β-actin gene promoter, wherein said modified chick β-actin promoter is a hybrid promoter formed by:

deleting a DNA fragment from the 3' end of said promoter, wherein said fragment (A) ranges from the middle of the intron of said promoter to a location downstream thereof and (B) comprises a splicing acceptor sequence, and linking to the 3' end of said promoter a DNA fragment containing an alternate splicing acceptor sequence.

2. The expression vector of claim 1, wherein said alternate splicing acceptor sequence is a DNA fragment containing a splicing acceptor sequence from a rabbit β-globin gene.

3. The expression vector of claim 1, wherein said expression vector further comprises at least one gene derived from *E. coli* for cloning said vector in *E. coli*.

4. The expression vector of claim 3, wherein said at least one gene is a drug resistant gene and/or a replication origin capable of functioning in *E. coli*.

5. The expression vector of claim 1, wherein said expression vector further comprises an SV 40 early transcription splicing sequence and a polyadenylation sequence.

6. The expression vector of claim 5, wherein said expression vector further comprises the SV 40 replication origin.

7. The expression vector of claim 1, wherein said expression vector further comprises the SV 40 replication origin.

8. A process for expressing an exogenous gene which comprises (a) incorporating said exogenous gene into an expression vector for the expression of an exogenous gene in an animal cell, the expression vector comprising a modified chick β-actin gene promoter and a restriction enzyme site for incorporating an exogenous gene downstream of said chick β-actin gene promoter, (b) introducing said vector into an animal cell and (c) culturing the resulting transformed cell, wherein said modified chick β-actin promoter is a hybrid promoter formed by:

deleting a DNA fragment from the 3' end of said promoter, wherein said fragment (A) ranges from the middle of the intron of said promoter to a location downstream thereof and (B) comprises a splicing acceptor sequence, and linking to the 3' end of said promoter a DNA fragment containing an alternate splicing acceptor sequence.

9. The process of claim 8, wherein said expression vector further comprises at least one gene derived from *E. coli* for cloning said vector in *E. coli*.

10. The process of claim 8, wherein said expression vector further comprises an SV 40 early transcription splicing sequence and polyadenylation sequence.

11. The process of claim 8, wherein said expression vector further comprises the SV 40 replication origin.

* * * * *